(12) United States Patent
Olson, Jr. et al.

(10) Patent No.: US 6,960,215 B2
(45) Date of Patent: Nov. 1, 2005

(54) TACTICAL DETACHABLE ANATOMIC CONTAINMENT DEVICE AND THERAPEUTIC TREATMENT SYSTEM

(75) Inventors: Stanley W. Olson, Jr., San Ramon, CA (US); Lex P. Jansen, Pleasanton, CA (US); Michael Burns, Boston, MA (US)

(73) Assignee: Boston Scientific SciMed, Inc., Maple Grove, MN (US)

(*) Notice: Subject to any disclaimer, the term of this patent is extended or adjusted under 35 U.S.C. 154(b) by 297 days.

(21) Appl. No.: 10/142,133

(22) Filed: May 8, 2002

(65) Prior Publication Data

US 2003/0212426 A1 Nov. 13, 2003

(51) Int. Cl.[7] .............................. A61B 17/70; A61F 2/44
(52) U.S. Cl. .............................. 606/92; 606/93; 606/53; 623/17.12
(58) Field of Search .................. 606/92, 93; 623/17.11

(56) References Cited

U.S. PATENT DOCUMENTS

| | | | |
|---|---|---|---|
| 4,364,392 A | 12/1982 | Strother et al. | |
| 4,904,267 A | 2/1990 | Bruce et al. | 623/23 |
| 4,969,888 A | 11/1990 | Scholten et al. | 606/94 |
| 5,015,256 A | 5/1991 | Bruce et al. | 623/18 |
| 5,217,496 A | 6/1993 | Bruce et al. | 623/16 |
| 5,234,437 A | 8/1993 | Sepetka | 606/108 |
| 5,250,071 A | 10/1993 | Palermo | 606/198 |
| 5,261,916 A | 11/1993 | Engelson | 606/108 |
| 5,304,195 A | 4/1994 | Twyford, Jr. et al. | 606/191 |
| 5,312,415 A | 5/1994 | Palermo | 606/108 |
| 5,350,397 A | 9/1994 | Palermo et al. | 606/200 |
| 5,571,189 A * | 11/1996 | Kuslich | 623/17.12 |
| 5,624,449 A | 4/1997 | Pham et al. | 606/108 |
| 5,643,089 A | 7/1997 | Hummel et al. | 464/37 |
| 5,876,116 A | 3/1999 | Barker et al. | 366/182.3 |
| 5,891,128 A | 4/1999 | Gia et al. | 604/104 |
| 5,961,211 A | 10/1999 | Barker et al. | 366/182.3 |
| 6,024,480 A | 2/2000 | Seaton et al. | 366/130 |
| 6,032,677 A | 3/2000 | Blechman et al. | 128/899 |
| 6,033,105 A | 3/2000 | Barker et al. | 366/182.3 |
| 6,165,178 A | 12/2000 | Bashiri et al. | 606/108 |
| 6,231,615 B1 | 5/2001 | Preissman | 623/23.73 |
| 6,235,043 B1 | 5/2001 | Reiley et al. | 606/192 |
| 6,238,415 B1 | 5/2001 | Sepetka et al. | 606/213 |
| 6,241,734 B1 | 6/2001 | Scribner et al. | 606/93 |
| 6,245,088 B1 | 6/2001 | Lowery | |
| 6,248,110 B1 | 6/2001 | Reiley et al. | 606/93 |
| 6,273,916 B1 | 8/2001 | Murphy | 623/23.62 |
| 6,280,456 B1 | 8/2001 | Scribner et al. | 606/192 |
| 6,299,627 B1 | 10/2001 | Eder et al. | 606/191 |
| 6,309,402 B1 | 10/2001 | Jendersee et al. | 606/198 |
| 6,312,405 B1 | 11/2001 | Meyer et al. | 604/96.01 |
| 6,375,668 B1 | 4/2002 | Gifford et al. | |
| 6,607,544 B1 * | 8/2003 | Boucher et al. | 606/53 |
| 6,740,093 B2 * | 5/2004 | Hochschuler et al. | 606/94 |

FOREIGN PATENT DOCUMENTS

| | | |
|---|---|---|
| DE | 196 10 333 A1 | 9/1997 |
| WO | WO 89/12472 | 12/1989 |
| WO | WO 99/02108 A1 | 1/1999 |
| WO | WO 99/37256 | 7/1999 |
| WO | WO 00/13615 | 3/2000 |
| WO | WO 00/64504 | 11/2000 |
| WO | WO 01/56486 A1 | 8/2001 |
| WO | WO 02/30338 A1 | 4/2002 |

* cited by examiner

*Primary Examiner*—Julian W. Woo
*Assistant Examiner*—Sarah Webb
(74) *Attorney, Agent, or Firm*—Bingham McCutchen LLP

(57) ABSTRACT

Devices and methods for the controlled delivery of therapeutic agents into bone and soft tissue to prevent the unintentional migration of therapeutic agents from the treatment site. The containment device can be made of a fabric or membrane that is porous, semi-porous, non-porous, bio-resorbable, or non-resorbable materials. A containment device is advanced to the interior of the target structure and filled with a therapeutic agent. The containment device may be permanently or temporarily implanted. Where permanent implantation is desired, the containment device may be detached via a severable junction.

11 Claims, 5 Drawing Sheets

TACTICAL DETACHABLE ANATOMIC CONTAINMENT DEVICE AND THERAPEUTIC TREATMENT SYSTEM

FIELD OF THE INVENTION

This invention relates to medical implants, and in particular, to detachable containment systems for implanting therapeutic materials in vivo.

BACKGROUND

Numerous bone conditions or spinal injury can cause painful collapse of vertebral bodies, including osteopenia (osteoporosis), vertebral hemangiomas, multiple myeloma, necorotic lesions (Kummel's Disease, Avascular Necrosis), metastatic disease and complications from steroid and non-steroidal anti-inflammatory drug (NSAID) use. Osteoporosis is a systemic, progressive and chronic disease that is usually characterized by low bone mineral density, deterioration of bony architecture, and reduced overall bone strength. Vertebral body compression fractures (VCF) are more common in people who suffer from these medical indications, often resulting in pain, compromises to activities of daily living, and even prolonged disability. Likewise, degenerative and injured spinal disk rehabilitation (pharmacological or gene therapeutic) protocols to delay the progression of intradiscal diseases, or even to restore disk health and disk functions, are a part of contemporary research developments and emerging standards of care.

The science of spinal intervention has made great strides in recent years. On some occasions, spinal or poly-trauma patients experience VCFs that may be repaired by vertebroplasty and other spinal reconstructive means. Vertebroplasty, which literally means fixing the vertebral body, has been used in the United States since the mid-1990s to treat pain and progressive deterioration associated with VCF. Most often in this vertebroplasty procedure, a bone cement, like opacified polymethylmethacrylate (PMMA), or other suitable biomaterial alternatives or combinations, is injected percutaneously into the bony architecture under radiographic guidance and controls. The hardening (polymerization) of the cement media or the mechanical interlocking of other biomaterials serve to buttress the bony vault of the vertebral body, providing both increased structural integrity and decreased potential for painful micromotion and progressive collapse of the vertebrae and spinal column.

Bone tamps (bone balloons or Kyphoplasty™), a contemporary balloon-assisted vertebroplasty alternative for treatment of VCF, also involves injection of a bone cement into a mechanically created bone void within vertebral body. In this alternative vertebroplasty procedure, a balloon tamp is first inserted into the structurally compromised vertebral body, often through a cannula. The bone balloon is then deployed under high pressure. The expanding balloon disrupts the cancellous bone architecture and physiological matrix circumferentially and directs the attendant bony debris and physiologic matrix toward the inner cortex of the vertebral body vault. The balloon tamp is then collapsed and removed, leaving a bony void or cavity. The remaining void or cavity is repaired by filling it with an appropriate biomaterial media, most often bone cement. In most cases, the treatment goals are to reduce or eliminate pain and the risk of progressive fracture of the vertebral body and its likely resulting morbidity, complications, and disability.

Although most of these interventional procedures are an improvement over previous conservative treatments that consisted of bed rest, pharmaceuticals, and/or cumbersome back braces, these methods still suffer from the complication of potential leakage of the therapeutic biomaterial repair media (bone cement, etc.) outside of the desired treatment zone. Numerous risks are associated with these spinal interventional procedures. The risks and complications, which are related to the leakage of the biomaterial into structures that are intended to be preserved, may involve extravasation of the biomaterial into veins and/or lungs, infections, bleeding, rib or pedicle fracture, pneumothorax, increased pain, a range of soft and/or neural tissue impingement, paresis, and paralysis. Most clinicians prefer to focus or contain treatments to the injured or diseased tissues alone.

Disease and injury can also erode or violate the supporting and collateral soft tissues. In the case of an insult, disruption, disease, or injury to a joint construct (spinal column [e.g., spinal facet], hip, knee, elbow, fingers, ankle, shoulder, synovium, collateral ligaments, etc.), joint capsule, ligamentous structures, or cartilaginous (collagen based) tissues, it may be necessary to manage or contain physiological biomaterial, or other therapeutic media within the joint or anatomic structure. Likewise, primary and secondary spinal tumors may contribute to a loss of tissue (bony, etc.) integrity and strength. Therefore, these tumors may serve as indications for vertebroplasty and other interventional spinal augmentation. The treatment of many other diseases of the bone and other tissues can also be facilitated by treating the diseases from within and/or proximate to the target anatomy. For example, chemotherapeutic agents could be implanted in proximity to or within a tumor. Or in the case of a failed bony fusion (pseudoarthrosis), a reoperation and revision may be avoided through the introduction of biological agents into a containment device designed to promote bony healing. In particular, bone healing by interventional means may be facilitated by the implantation of osteophilic (osteoinductive or osteoconductive) materials, which are scaffolds and/or materials used to stimulate or optimize bony healing. These materials include, but are not limited to, hydroxylapaptite (HA), tri-calcium phosphate, biocoral, bioceramics, biomaterial granules, demineralized bone matrix (DBM), bone morphogenic proteins (BMPs), and collagen. Bone morphogenic proteins (BMPs), an active ingredient in DBM and a member of the TGF-β (transforming growth factor-β) super family, mediate developmental processes that include morphogenesis, differentiation, cell survival, and apoptosis. Although the role of TGF-β is not fully understood, its net effect is an increase in bone matrix. Other factors, such as insulin-like growth factors (IGF I and IGF II) and platelet derived growth factor are also important. Unfortunately, since these proteins have short biological half-lives, they must be maintained at the treatment zone in sufficient therapeutic concentrations in order to be effective. Therefore, dilution of the therapeutic agent due to the unintentional migration of the implanted material away from the therapeutic zone is also a major challenge to good patient outcomes.

Accordingly, it would be desirable to provide treatment systems and methods that contain and deliver implanted biomaterial or other pharmacological or treatment media at any time during the treatment cycle, while preventing the unintentional migration of the implanted materials and/or controlling the release of the implanted materials into the targeted tissue or cellular treatment zone.

SUMMARY OF THE INVENTION

This invention relates to medical implants, and in particular, containment systems for implanting therapeutic materials in vivo. The containment device of the present invention is especially appropriate, but not limited to VCF treatments. The containment device provides a barrier, preventing the unintentional migration of its augmentation, reconstructive, pharmacological, and therapeutic contents from the treatment site. In one embodiment, the containment device is an appropriately compliant, mechanically expandable, or self-expandable containment structure that can be filled with selected therapeutic materials. Alternatively, the containment device could be made of a semi-compliant or rigid material, as may be the case with many spinal fusion implants. The material used to construct the containment or channeling device may be porous, semi-porous, non-porous, bio-resorbable, or non-resorbable, depending on the therapeutic objective. The material may also be made from a continuous material with uniform properties, a fenestrated material, or a material having a variable thickness to achieve specified geometric deployment. The containment device may have many shapes depending on the structure to be treated and the intended therapeutic effect. These include, but are not limited to, a "pouch" that can be sealed, a "stent" to channel or direct the therapeutic material, an elongated "sausage"-like shape, or a flattened "disk"-like shape. In addition, a particular embodiment may include a double- (or multiple) nested containment device, where there is at least one containment device nested within another. The containment device may be filled with a variety of therapeutic agents, depending on the therapeutic objective. In the case of VCFs, the containment device may preferably be filled with a bone cement, such as PMMA or the like, or an osteoconductive or osteoinductive material. In the case of tumors, whether in bones or soft tissue, chemotherapeutic agents may be injected into the containment device.

In a vertebroplasty operation, the containment or channeling device is inserted into the interior of the vertebral or other bony body through a hole in the exterior of the bone. The device is then deployed into the interior of the structure and filled with the desired therapeutic material. The device can be deployed by a variety of mechanisms, including response to temperature change, mechanical mechanisms, or deployment by a suitable gas. Alternatively, the containment or channeling device may be self-expanding, assuming its secondary shape automatically upon release from the delivery device. In the case of a VCF, the therapeutic material utilized is often PMMA or some other bone cement. The device can then be sealed, using a variety of methods, if desired.

Depending on the therapeutic objective, the containment or channeling device can be accessorized accordingly. The device may be made detachable where permanent implantation is desired. A wide variety of detachment technologies are known in the art. Preferably, an electrolytic detachment technology, using a braided catheter, may be used to separate the containment and delivery devices after the containment device is filled. The device may also be retrievable where only temporary implantation is needed.

In addition, the containment or channeling device may also be combined with other external or internal systems to monitor healing and/or stimulate therapeutic responses. For example, some device and environmental controls may include, but are not limited to, phototherapeutic modalities, temperature modulation, electrical stimulation, and electromagnetic fields.

BRIEF DESCRIPTION OF THE DRAWINGS

Preferred embodiments of the present invention are illustrated by way of example, and not by way of limitation, in the figures of the accompanying drawings, in which like reference numerals refer to like components in which.

DETAILED DESCRIPTION OF THE PREFERRED EMBODIMENTS

Figure 1A:
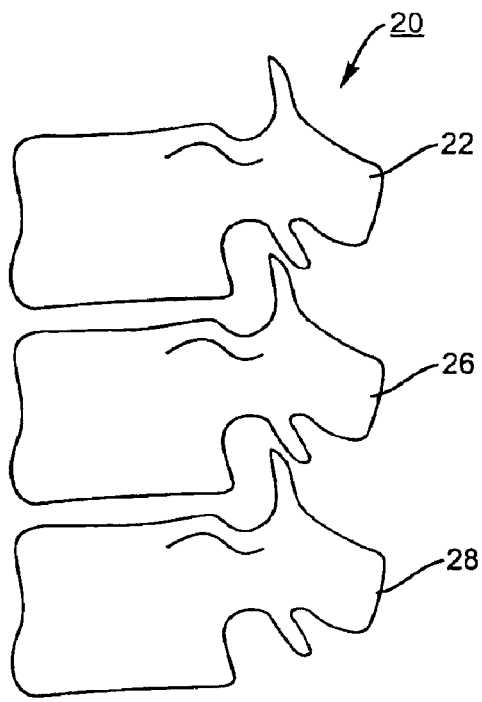
FIG. 1A is a lateral view of three normal vertebrae.
Figure 1B:
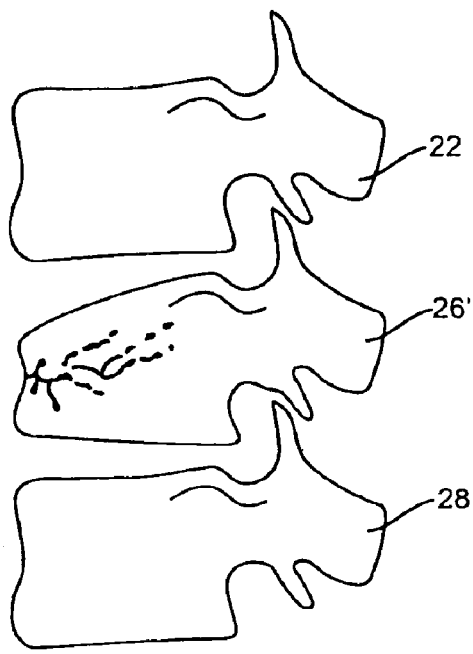
FIG. 1B is a lateral view of three vertebrae wherein the vertebral body of the middle vertebra is compressed.

Turning to FIG. 1A, the lateral view of typical spinal motion segments 20 are depicted, with lumbar vertebrae 22, 26, and 28. In contrast, FIG. 1B illustrates a lateral view of a segment of a spinal column in which the middle vertebra 26' is compressed. Compression can result from conditions such as osteoporotic fractures, malignant metastatic disease, and benign tumors of the bone and are suitable for treatment using the present invention.

Figure 2:
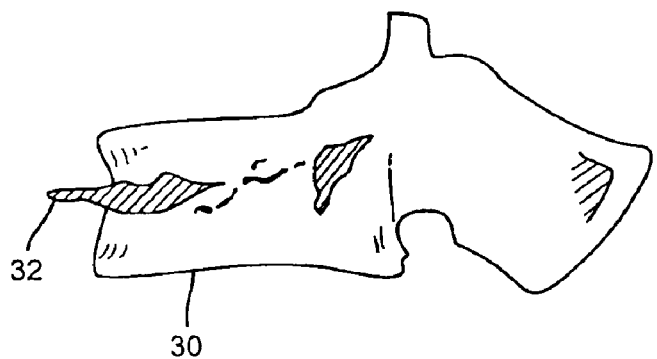
FIG. 2 is a lateral view of a compressed vertebra with bone cement extruded through the fractured vertebral vault.

The percutaneous injection of bone cements, such as PMMA or the like, in vertebroplasty and kyphoplasty procedures has had some success in the treatment of pain associated with VCFs commonly found in osteoporosis patients. The bone cement is believed to solidify the porous inside and/or potential fractures on the outside of the vertebral body. When effectively injected, the bone cement is thought to prevent painful motion of the bony segments and to strengthen the spinal column to prevent further degradation and collapse. Leakage of the bone cement outside of the preferred treatment zone, however, not only does not alleviate the pain but can also lead to serious side effects. As seen in FIG. 2, where bone cement has extruded through the fractured vertebral vault 30, an exposed, sharp, abrasive, and durable surface 32 may be formed. This extruded media could erode nearby anatomic structures, causing further pain and complications. The precise direction, placement, and containment of therapeutic media and agents is fundamental to optimal patient outcomes. Iatrogenic injury may be reduced or eliminated by the proper application of a containment or channeling technology. The present invention tends to prevent the unintentional migration of implanted materials, such as bone cement, from the treatment site. This invention, however, is not limited to the treatment of fractures in the vertebra. The containment device may be utilized in any other bone or soft tissue where it is desired to control either the release or the unintentional migration of a therapeutic agent. Moreover, it may be utilized to concentrate therapeutic agents at the treatment site, resulting in their improved biomechanical function and/or therapeutic effect.

1. The Device

Figure 3:
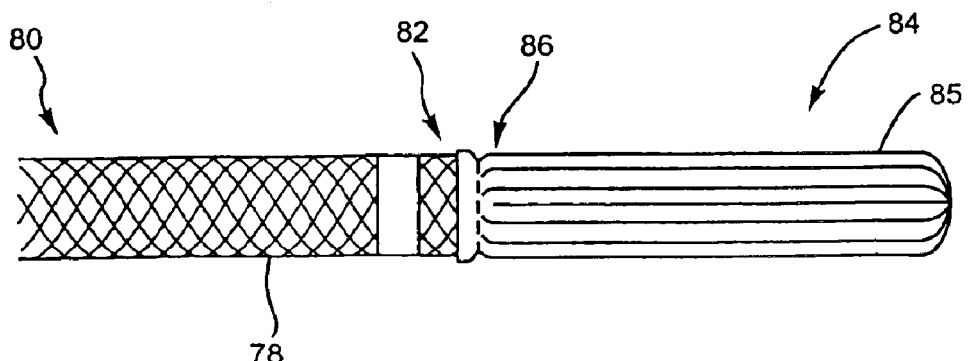
FIG. 3 is a top view of a probe including a catheter tube with an expandable structure in a substantially collapsed condition attached to the distal end of the catheter.

The containment or channeling device of the present invention is a generally hollow or fillable body that concentrates the focus of the therapeutic agent and reduces or prevents unintentional migration of therapeutic materials from the interior of the containment or channeling device into tissues or voids that are intended to be preserved. As depicted in FIG. 3, one embodiment of the device 84 includes a fillable or expandable body 85 made from a relatively soft, flexible material. The shape of the device will depend upon the therapeutic objectives surrounding its use and the conformity tolerances of the tissues being treated. In many cases, where the wall of the containment or channeling device is made from a relatively soft, flexible material, such as a fabric or a membrane, the containment device 84 could conform to the cavity inside of the vertebral or other bony body or soft tissue being treated. Alternatively, the device may be made of a semi-compliant or rigid material having a pre-determined shape. The containment or channeling material may be porous, semi-porous, non-porous, bioresorbable, or non-resorbable. It may be made from a continuous material with uniform properties or it may be interrupted or fenestrated to achieve the treatment objectives. In some instances the materials may have a variable thickness or durometer (hardness) to achieve specialized geometric deployment. For example, a device material may be produced to allow geometric locating or anchoring protrusions from nominal surfaces of the containment device. In addition, self-expanding devices that rely on the design and biomaterial state of the art may be beneficial in some instances. The specialized properties of memory metals, memory polymers, and other suitable materials may contribute to the deployment and/or shaping of such a containment or channeling device.

Depending on the tissue to be treated and the intended therapeutic effect, the containment or channeling device may be many different shapes. Some embodiments may serve a directional or containment function by directing, channeling, or concentrating the treatment media within a specific anatomic orientation or structure or into a target treatment area. In such a case, the self-expanding device may be closed like a "pouch" that can be sealed after filling or open like a "stent" to channel the material more precisely.

One particular embodiment may self-expand, similar to a stent, and assume the geometry of a curved column (similar to a sausage casing or linked sausage casings), with either a closed or open end, that could serve to capture and/or channel the therapeutic media to achieve an optimal medical outcome. For example, the physician could carve out a curved void in the anterior region of the vertebral body and then deploy the elongated, curved device into the cavity. Where the device has at least one open end, e.g., similar to a curved hollow tube, the therapeutic media would leak out the open ends of the device, coming into contact with the cancellous bone along the lateral edges of the verteberal body. Although the therapeutic media, e.g., bone cement, would subsequently invade the interstices of the cancellous bone, the containment channel would still serve its intended purpose by preventing the bone cement from entering the venous plexus.

Figure 7A:
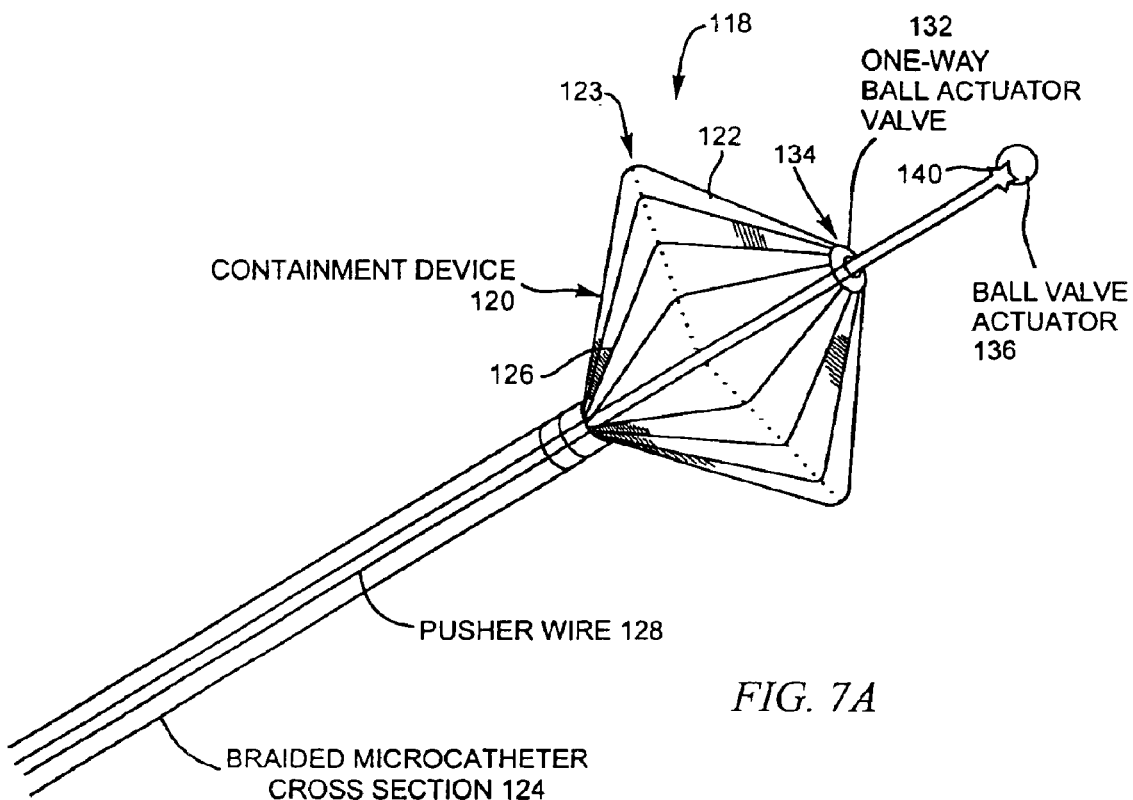
FIG. 7A is a side-view of a self-expanding containment device.

In another embodiment, as seen in FIG. 7A, the containment or channeling device 120 may have a bulbous geometry that could be manipulated to assume alternative shapes as it conforms to the anatomy where it is inserted. During or after deployment of the device, application of an external force could cause the containment device, which may comprise memory metals or memory polymers, to deform plastically into the shape or space of the tissues that are to be treated. For example, as depicted in FIG. 7C, after filling with the therapeutic material, the containment device 120 may be collapsed to assume a concave disk-like geometry 120'.

Another desirable embodiment may be a double (or multiple nested) containment device where there are at least two devices, nested within each other. In this embodiment, one containment device would surround the other and each would be capable of being filled with a therapeutic agent. For example, in the treatment of a soft tissue lesion (e.g., tumor, etc.), it may be beneficial to have an inner containment device with a structural material to provide load-bearing support, while filling the outer containment device with a chemotherapeutic agent. In this manner, as the lesion responds to chemotherapeutic agent and "shrinks," the structural material could remain intact to support the tissue that remains.

Many different delivery devices may be used in conjunction with the containment or channeling device, enabling the placement of the containment device in the proper treatment site. These include, but are not limited to, a catheter, cannula, needle, syringe, or other expandable delivery device. For example, one embodiment of the invention, as shown in FIG. 3, includes a catheter 78 having a proximal end 80 and a distal end 82. A proximal end 86 of a flexible containment device 84 is attached to the distal end 82 of the catheter 78 in an appropriate manner, e.g., cyanoacrylate glue (or other appropriate adhesive) or construct welded joints (metallic and non-metallic), that may best serve any desirable detachment system. These detachment systems include any joint severable by electrolytic, mechanical, hydraulic, photolytic, thermal, or chemical means.

A wide range of materials can be placed into or, alternatively, coated onto the outside of the containment or channeling device. Bone cement, such as PMMA or the like, could be injected into the containment device 84 to treat compression fractures in the vertebral bodies. Likewise, any number of polymer or liquid formulas, properly contained or channeled, may serve the therapeutic requirements equally well. The biomaterial need only be adapted to physiology, which is primarily its viscoelastic and strength requirements, suited to the fit, form, and function of the treated structures and clinical outcome requirements. Where the wall of the containment or channeling device is formed from a non-porous material, the device could prevent the material, e.g., PMMA or epoxy, from "leaking" outside of the vertebra. In the alternative, if the wall is formed from a porous material, either rigid or flexible, the implanted materials may migrate or diffuse away from the containment device into the surrounding area. For example, where the containment device contains large pores, it may be filled with bone cement, such as PMMA or the like, possibly under pressure, until the device reaches its maximum capacity. The bone cement may then begin to seep out of the pores to form protrusions in the form of bumps or rods of bone cement extruding in an unorganized manner from the containment device. In addition to filling any remaining voids in the cancellous bone of the vertebral body, the extruded spikes may aid in anchoring the containment device in its proper therapeutic place, even if the vertebral body later changes shape due to further deterioration. In light of the progressive deterioration of bones seen in diseases such as osteoporosis and cancer, these extruded rods could provide much needed continued support even after the bone resorbs.

In addition to bone cements, other therapeutic materials may also be injected into the containment device. Where the containment device is made from porous or semi-porous materials, the therapeutic agents may escape or diffuse through the pores into the surrounding environment. The appropriate degree of porosity or permeability could be determined in order to achieve the correct dosing and may depend in part on the concentration of the therapeutic agent and the size of the treatment site. Similarly, the containment device may serve as a time-release or dosing vessel in delivering the therapeutic agent where a bio-resorbable material, such as poly-lactic acid (PLA), is used. In the treatment of fractures, osteoconductive materials, which provide scaffolds on which new bones can grow, and osteoinductive materials, which activate stem cells to promote and/or induce bone formation, would be useful in treating compression fractures and enhancing bone growth. Possible therapeutic materials to be placed in the containment device include, but are not limited to, bone cements and other autogenous tissues or cells, donor tissues or cells, bone substitutes, bone morphogenic proteins (e.g., BMP-2 or OP-1), growth factors (e.g., TGF-β, IGF I, IGF II, and platelet-derived growth factor), tissue sealants, chemotherapeutic agents, and other pharmaceutical agents.

Figure 4A:
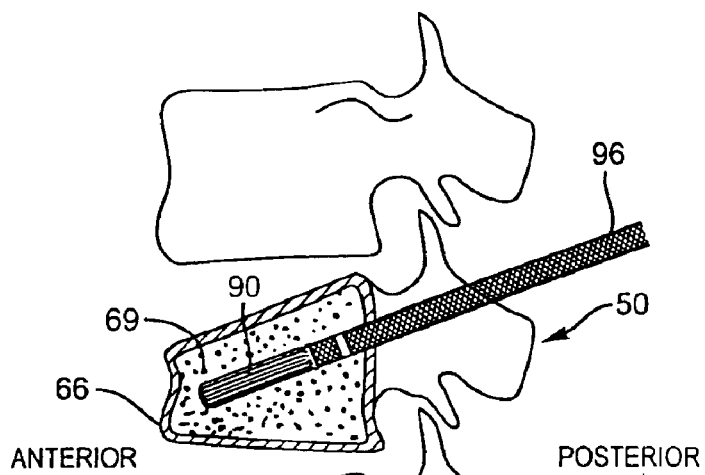
FIG. 4A is a lateral view of a transpedicular placement of the a representative expandable containment device into a damaged vertebra.
Figure 4B:
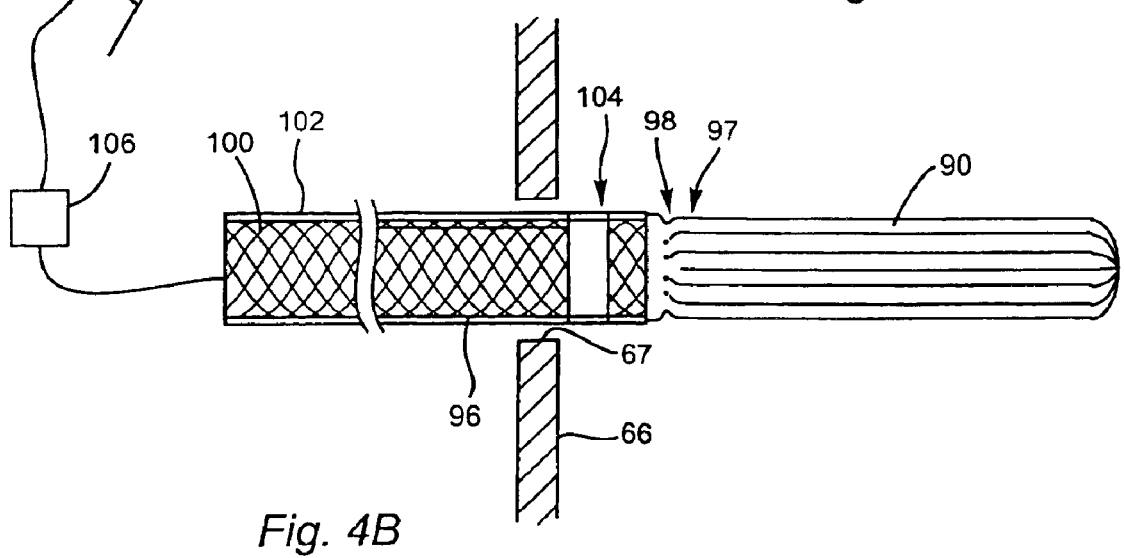
FIG. 4B is a vertical section through a vertebral bone showing an attached containment device in a substantially collapsed condition attached to the distal end of a catheter with a severable electrolytic joint.

Depending on the patient's condition, the physician may choose to modify or accessorize the containment or channeling device as needed. For example, the device may be permanently or temporarily implanted. FIGS. 4A and 4B depict the device 90 inserted through a hole 67 in the cortical bone 66 of a lumbar vertebra 50. Where the device 90 is to be implanted in the patient permanently, various detachment technologies may be employed after the containment or channeling device and therapeutic agents are delivered to the proper treatment site. Alternative detachment means may include, but are not limited to, electrolytic detachment; mechanical interference fit (Morse-taper-type, and the like) that can be detached by hydraulic technologies, ball valves, gas pressure changes; breakaway designs (severable by force or exposure to an alternate internal or external technology); photolytic means (severable by exposure to light, laser, and the like); thermal modulation (heat, cold, and radio frequency); mechanical means (screwing/unscrewing); and bioresorbable technologies (severable by exposure to an aqueous solution such as water, saline, and the like).

In one embodiment, the containment or channeling device 90 could be detached from delivery device 96 using a mechanical interference fit that can be detached by hydraulic technologies. For instance, a pressure could be applied by means of a syringe to a mechanically (friction) locked mandrel inside a tube, which is filled with a mechanically compatible liquid. The tube could extend from the detachment area to the proximal end of the containment or channeling device 90.

In another embodiment, the containment or channeling device 90 could be detached using thermal or photolytic means. A heat or light source at the detachment area could be in contact with the material connecting the proximal end of the containment or channeling device 90 and the delivery device, melting it to the point of disconnecting the containment or channeling device 90. Examples of heat or light sources include, but are not limited to, a current through a resistance wire, a laser provided through fiber optic means, or the like.

In another embodiment, the containment or channeling device 90 could be detached through mechanical means. This could include various designs of interlocking ends that are held together by a sleeve. Different types of mechanically deployable joints that may be adapted for use with the containment or channeling device 90 are described in U.S. Pat. Nos. 5,234,437; 5,250,071; 5,261,916; 5,304,195; 5,312,415; and 5,350,397, the entirety of which are herein expressly incorporated by reference.

In yet another embodiment, the containment or channeling device 90 could be detached from a delivery device 96, such as a braided catheter, that is electrolytically conductive. The use of electrolytically detachable joints, attached to solid or braided (plurality of filaments) pusher wires, hypotubes, or braided catheters may increase physician control during insertion, navigation, deployment, detachment, and retrieval. As seen in FIG. 4B, the proximal end 97 of the device 90 could be attached to the distal end 98 of the braided catheter 96 in an appropriate manner. For example, a cyanoacrylate glue (or other appropriate adhesive) or a construct welded joint (metallic and non-metallic), may be used to attach the containment or channeling device 90 to the distal end 98 of the braided catheter. In general, the entirety of the braided catheter 96 is coated with an insulating material 102 from its proximal end 100 continuously to the electrolytically severable junction 104. Insulating material may include, but is not limited to, polytetrafluoroethylene (e.g., Teflon), polyparaxlylene (e.g., parylene), or polyethyleneterrephthalate (PET), polybutylenoterephthalate (PBT), cyanoacrylate adhesives, or other suitable insulating layers. The electrolytically severable junction 104, devoid of insulating material, is therefore much more susceptible to electrolysis in an ionic solution such as blood or most other bodily fluids. The proximal end 100 of the braided catheter 96 may also be left bare so that a power supply 104 may be attached, which may provide power for electrolysis of the joint. The other pole of the power supply is typically attached to a patch on the skin 108 to complete the circuit. After the containment or channeling device is placed in the treatment area and filled with a therapeutic agent, the device may be severed from the braided catheter used in delivery by the application of a small electrical current to the braided catheter 96.

When necessary, many different methods may be used to seal the containment device. In one embodiment, the containment device may contain a self-sealing one-way valve. In another embodiment, a plug, such as a detachable silicone balloon, may be used to seal the neck of the containment device. In the case of the electrolytic detachment using the braided catheter, for example, a detachable silicone balloon may be used to plug the catheter distal of the severable joint and proximal to the containment device. In yet another embodiment, the containment device may adhere to itself where it is made from a material with appropriate adhesive and/or elastic properties, thereby sealing the contents inside. In addition, where a bone cement such as PMMA or the like, or a similar substance that solidifies over time, is impregnated in the containment device, the hardening of the bone cement within the containment device after sufficient time has passed obviates the need for an additional seal. These examples of sealants are not meant to be limiting; any other sealant method known to those who are skilled in the art may be employed to close the containment device and prevent the unintentional migration of its contents from the treatment site.

Where the device or a portion of the device is only intended to be implanted temporarily, the device may be collapsed and subsequently removed from the body after the contents of the containment device have substantially migrated outside of the device or when it is desired. In order to facilitate navigation, detachment, removal, and implantation of the containment or channeling device, all or portions of the surfaces of the access, delivery, and containment devices may be modified. Surface modifications and methods may include, but not be limited to, ion bombardment, physical vapor deposition plasma coatings, water-soluble neuroprotectant or vascular protectant coatings (heparin, etc.), hydrophilic coatings, anti-adhesion coatings, peptide coatings, gene therapy treatments, anti-corrosion coatings, electrically insulating coatings, or other technologies as known in the art. These coatings may prevent further injury to the patient while the device is being removed since the coating may decrease the risk of scar tissue forming around the implanted foreign devices. As is well-known to one skilled in the art, any number of surface modifications may complement the utility of the device applications and outcomes. In addition, retrievable containment or channeling devices may utilize different delivery systems than those used in the case of detachable devices. In particular, catheters capable of electrolytic detachment may not be chosen in order to avoid the possibility of accidental detachment due to unintentional exposure of the electrolytic joint to an ionic environment.

In alternative embodiments, additional materials that enhance the delivery and therapeutic effect of the agents may also be impregnated in the containment device. These include, but are not limited to, hydrogels, hydrophilic coatings, anti-adhesion media, peptides, and genes. For example, proteins such as BMP and TGF-β are known to enhance fracture healing, but have short biological half-lives. Therefore, maintaining these proteins at the fracture site in therapeutic concentrations has been problematic in the past. Delivering genes encoding for a given growth factor in a controlled manner to the fracture site may help overcome this problem. Through the use of a porous, semi-porous, or bio-resorbable containment devices, the genes encoding for BMP or TGF-β could be released into the treatment site and taken up by recipient cells that might then produce the growth factor at the fracture site; protein concentrations may then be able to be maintained for an extended period of time.

The containment or channeling device may also be combined with device or environmental stimulation to provoke or achieve the desired deployment effect and therapeutic response. For example, some device and environmental controls may include, but not be limited to, phototherapeutic modalities, temperature modulation, electrical stimulation, and electro-magnetic fields. For example, where a magnet is implanted in the containment device, application of a magnetic field may cause the implant to oscillate or may attract a magnetic media to fill the containment device. Under appropriate conditions, this micromotion may induce current to flow through the implant, ultimately resulting in enhanced bone growth and/or pain reduction. In an alternative embodiment, the containment device may be filled or coated with an electroconductive material associated with a power supply. When combined with an external controlling device to communicate with the power supply, the resulting current may enhance bone growth or other desirable tissue responses.

2. Methods of Use

Figure 5:
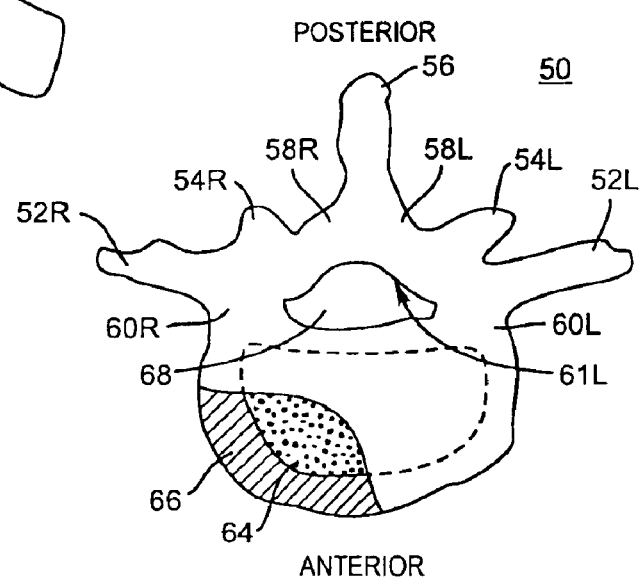
FIG. 5 is a top view of a lumbar vertebra, partially cut away.

Although, as noted above, use of the containment or channeling device of the present invention is not limited to treatment of vertebral ailments, such procedures are discussed here for exemplary purposes. Before discussing such methods of operation, various portions of the vertebra are briefly discussed. FIG. 5 depicts a top view of a vertebra 50. At the posterior of the vertebra are a right and left transverse process 52R, 52L, a right and left superior articular process 54R, 54L, and a spinous process 56. The right and left lamina, 58R, 58L, lie in between the spinous process 56 and the superior articular processes 54R, 54L, respectively. A right and left pedicle, 60R, 60L, are positioned anterior to the right and left transverse process, 52R, 52L. A vertebral arch 61 extends between the pedicles 60 and through the lamina 58. A vertebral body 62 is located at the anterior of the vertebra 50 and joins the vertebral arch 61 at the pedicles 60. The vertebral body 62 includes an interior volume of reticulated, cancellous bone 64 enclosed by a compact, cortical bone 66 around the exterior. The vertebral arch 61 and body 62 make up the spinal canal, i.e., the vertebral foramen 68; the opening through which the spinal cord and epidural veins pass.

Figure 6A:
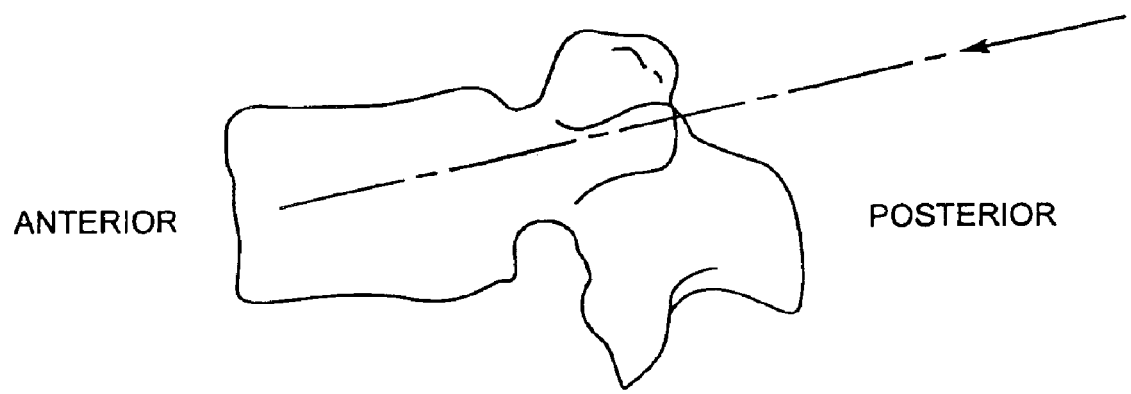
FIG. 6A is a lateral view of one posterior access route to the anterior vertebral body shown in FIG. 1.
Figure 6B:
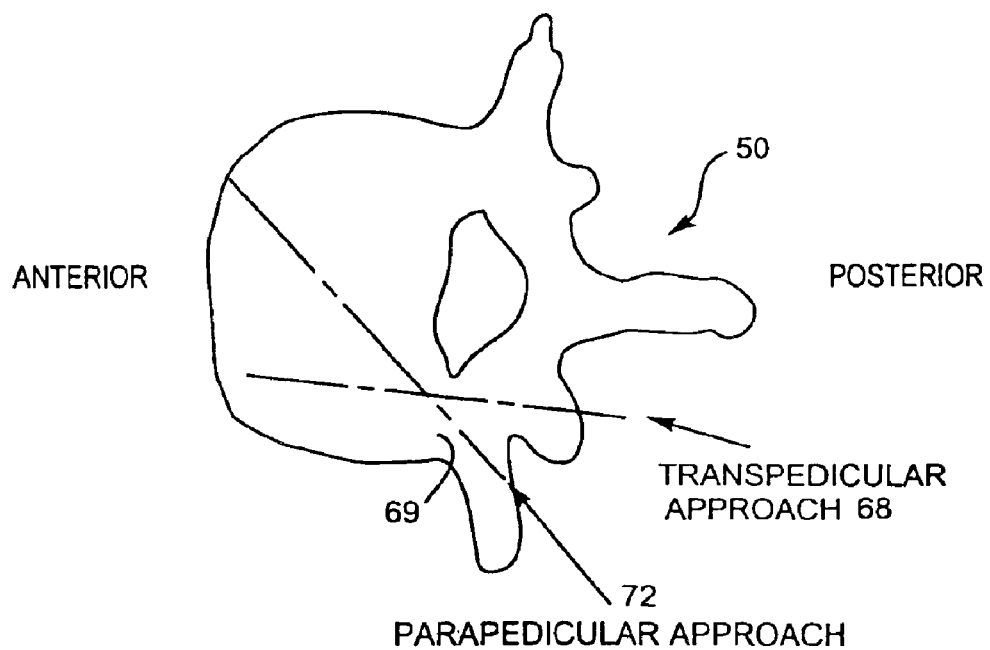
FIG. 6B is a top view of transpedicular and parapedicular routes to the anterior vertebral body.

As shown in FIGS. 4A and 4B, the present invention includes a detachable containment device 90 mounted on a delivery device 96 that is used to position, deploy, and fill the containment device 90. The physician can choose from a variety of approaches to insert the containment device into the vertebral body. As depicted in FIG. 6A, in the transpedicular approach 68, access to the cancellous bone 64 in the vertebral body 62 is gained through the pedicle 60. Alternatively, as depicted in FIG. 6B, a parapedicular approach 72 may be used in which access is gained through the side of the vertebral body 62 beside the pedicle 60. This approach may especially be chosen if the compression fracture has resulted in collapse of the vertebral body below the plane of the pedicle. Still other physicians may opt for an intercostal approach through the ribs (not shown) or a more clinically challenging anterior approach (not shown) to the vertebral body.

The method of the present invention further includes gaining access to the interior of the vertebral body 62 through a naturally occurring bore or passage 67 in the vertebra formed as a result of the condition to be treated, as seen in FIG. 4B. Alternatively, a bore or passage 67 in the bone may be formed with a drill. In the case of a flexible containment or channeling device 90, the size of the bore or passage 67 into the interior of the vertebral body 62 should be slightly larger than the external diameter of the implant body in its relaxed or pre-deployed state so that the containment device can be inserted through the bore into the vertebral body 62. Alternatively, where the containment or channeling device 90 is made from a semi-compliant or rigid material, the size of the bore or passage 67 must be slightly larger than the size of the external diameter of the semi-compliant or rigid implant. Depending on the level of deterioration of the vertebral body 62, the depth of the bore or passage 67 may also need to be sufficient to allow for the insertion of the full axial length of the device 90 into the vertebral body 62. In addition, the physician may further create a cavity 69 within the vertebral body 62 before insertion of the device 90 if desired. This may be accomplished using any surgical tool to carve out a cavity or perhaps by using an additional expandable or deployable device, such as those used in angioplasty or atraumatic tissue expansion or dissection. The containment device is preferably placed in the center of the vertebral body void or vault 62 in order to distribute support evenly to the entire structure and to the physiological loads typical a living organism.

As discussed before, the containment or channeling device may be delivered to the treatment site using many different delivery devices including, but not limited to, a catheter, cannula, needle, syringe, or other expandable delivery device. In one embodiment, the containment or channeling device 90 may be delivered to the treatment site via a guide sheath (not shown) through which the braided catheter 96 with the attached flexible containment or channeling device 90 in a substantially collapsed condition, may be pushed through the guide sheath to the interior of the bony body, the guide sheath having been combined with an obturator or the like, and tunneled through intervening tissue to gain access to the treatment site. The guide sheath may be retracted towards its proximal end, thereby releasing the device 90 into the interior of the vertebral body or other treatment site. Many delivery devices and methods could be employed to deliver the containment device to the treatment site and are well known to those who are skilled in the art.

Once the containment device 90 is placed in the proper treatment area, it can be filled or deployed in many ways. In one embodiment, wherein the device 90 is made from a flexible material, the device 90 may be deployed first in response to temperature change, mechanical release into the tissues, or with a suitable gas, such as carbon dioxide, and subsequently be filled with the desired therapeutic agent. For example, where a semi-porous material is used, carbon dioxide at an appropriate pressure may deploy the containment device 90, possibly creating a cavity within the cancellous bone, depending on the degree of deterioration of the vertebral body and the gas pressure used to deploy the containment device 90. The gas may subsequently escape through the pores prior to or while the containment device 90 is filled with the therapeutic material. The device 90 may also be deployed using any appropriate mechanical mechanism. This mechanical mechanism may be such that the containment device 90 may displace portions of the cancellous bone within the vertebral body upon deployment to create a cavity before it is filled with therapeutic materials. Alternatively, the device 90 could be filled directly with the therapeutic agent, possibly under pressure.

Where the containment or channeling device is self-expanding, similar to a stent, upon release from the guide sheath, the containment device may assume its primary shape within the cavity or void in which it is placed without the aid of any external forces. The device could subsequently be filled with the desired therapeutic material.

In an alternative self-expanding embodiment, the original shape of the device could be manipulated into another secondary shape with the application of an external force. As seen in FIG. 7A, a bulbous containment device 120, which includes memory metal or memory polymer that adds to its shape, is pushed through the distal end of a delivery catheter 124, here depicted as a braided microcatheter, by a pusher wire 128. The containment device 120 contains a one-way ball valve 132 on its distal end 134, which can be sealed by the ball valve actuator 136 located on the distal end 140 of the pusher wire 128. Under image guidance, the containment device assembly 118, which includes the containment device 120, pusher wire 128, and delivery microcatheter 124, is advanced through the guide sheath (not shown). As the containment device assembly 118 exits the guide sheath (not shown), it is navigated through the tissue or tissue void to be treated. The containment device 120 is constrained in its undeployed state within the inner lumen of the braided microcatheter 124 until final anatomic positioning is achieved. The pusher wire 128 is then advanced, pushing the containment device outside of the braided delivery catheter. As seen in FIG. 7A, the containment device, which is made from a self-expanding construct including memory metals and/or memory polymers or their performance equivalent, expands into the anatomy to be treated.

Figure 7B:
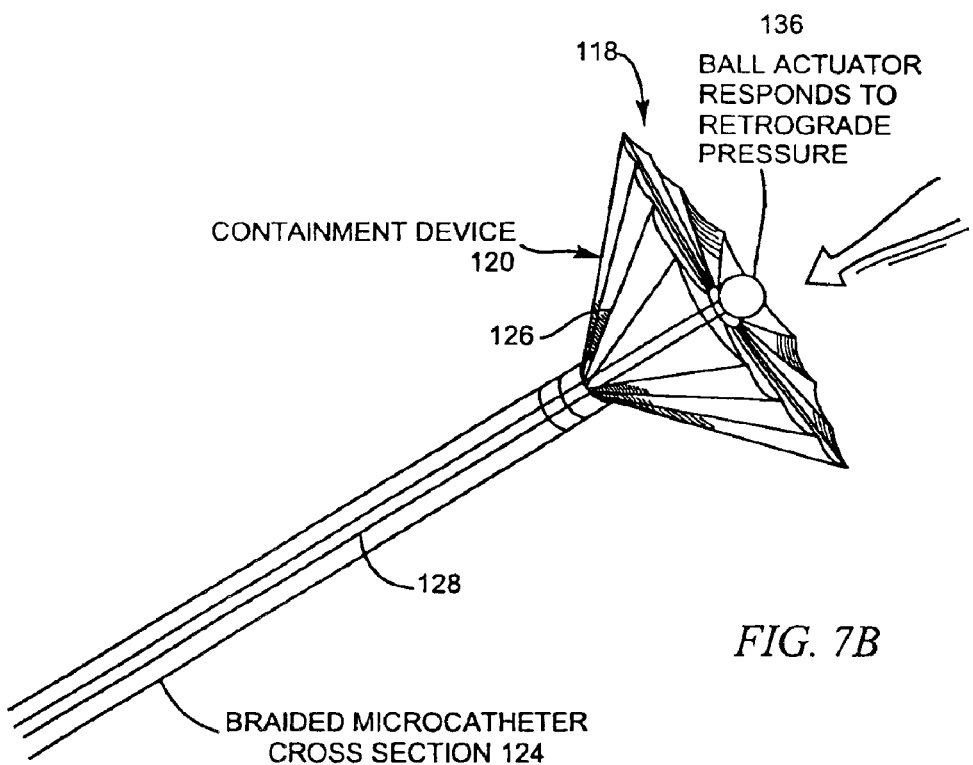
FIG. 7B is a side-view of the self-expanding containment device being deformed by a ball valve actuator.
Figure 7C:
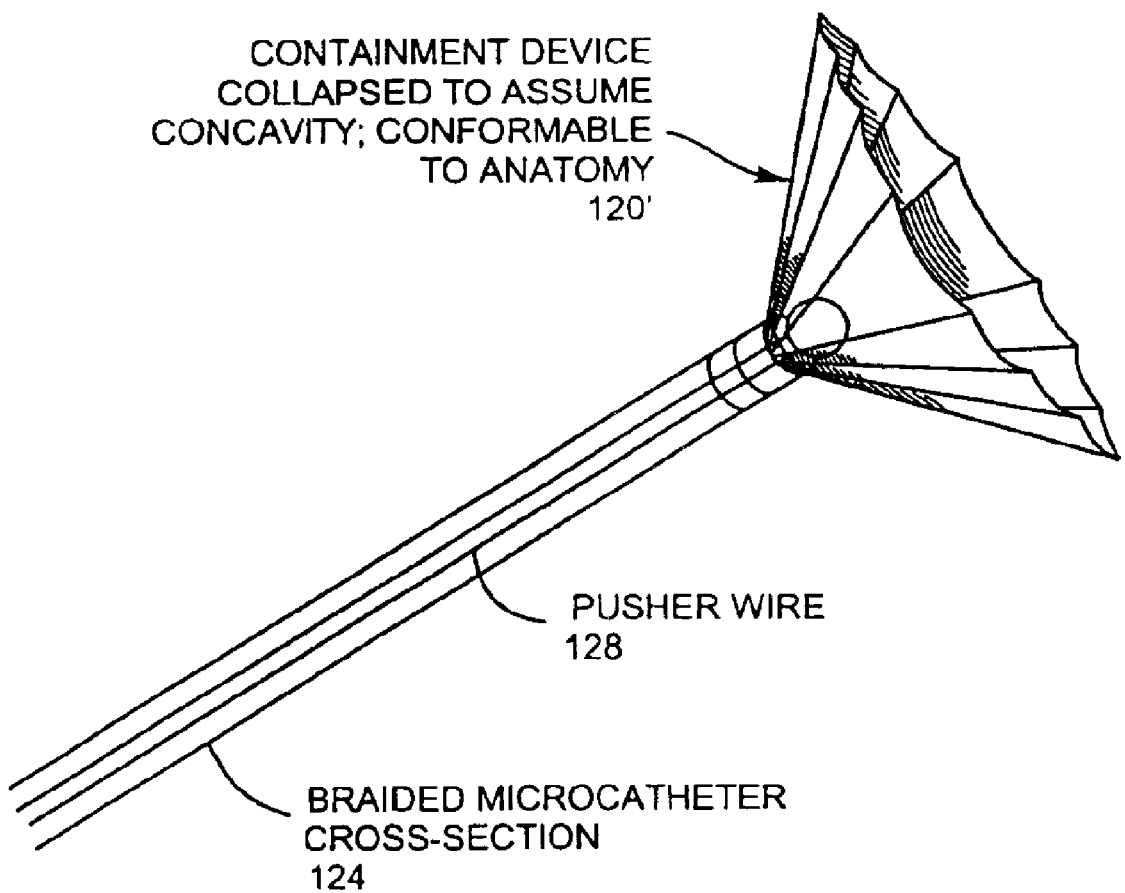
FIG. 7C is a side-view of the self-expanding containment device deformed by the ball valve actuator to assume a concave shape.

FIG. 7B depicts the shaping process of the containment device 120 as the ball actuator 136 engages the dome 122 of the containment device 120. The pusher wire 128, with its ball actuator 136, is used to begin the shaping of the device by applying a retrograde motion, as if to withdraw the pusher wire 128 from the delivery microcatheter 124. As the pusher wire 128 is pulled, the ball actuator 136 engages the ball valve 132 at the distal end 134 of the dome 122 of the containment device 120. The force of this motion plastically deforms the dome 122 of the containment device 120, pulling it towards the equator 123 of the containment device 120, ultimately to reshape the containment device 120 into a concave geometry, appropriate to the anatomy to be treated. Other means to deform or shape the device include, but are not limited to, changes in temperature or the application of an electrical or magnetic field.

The net effect of this action, as seen in FIG. 7C, is to deform the armature 126 sufficient to permanently remodel the containment device 120' geometry in a manner that improves the acceptance of the biomaterial or pharmaceutical agent and ultimately the therapeutic outcomes. The dome 122 of the containment device 120 has been drawn into its base. The armature 126 has reached its plastic deformation point without compromise to the ability of the containment device to contain any therapeutic media. The remodeled shape of the containment device (disk-like or bowl-like shape) may enable the treatment of tissues that benefit from this shape alternative.

In addition, other ailments, which are not specific to bone, may also be treated with the present invention. For example, in the case of cancer, whether it be in the bone or soft tissue, placement of a containment device into or near the tumor could allow for the delivery of chemotherapeutic agents directly to the tumor. Where the containment device is made from porous, semi-porous, or bio-resorbable material, the chemotherapeutic agents contained within the containment device may be able to diffuse to the surrounding area. The containment device may be placed inside of a tumor using an appropriate interventional technique. For examples, a guide sheath may be used to tunnel through adjacent tissue. The containment device may then be inserted into the desired therapeutic site through the guide sheath. When necessary, the containment device may be attached to the soft tissue. Sutures, or other methods that are well known to those who are skilled in the art, may be used to stabilize the placement of the containment device. Possible chemotherapeutic agents include, but are not limited to; cisolatin, doxcrubicin, daunorubicin, methotrexate, taxol, and tamoxifen. And in the case of deep wounds, the containment device may be used to deliver antibodies to the site. Additionally, it is conceivable that, myofascial pain syndrome, which is a condition of the tissues characterized by intense localized pain coming from muscles and their respective connective tissues, could also be treated. A containment device made from porous, semi-porous, or bio-resorbable material may be placed in between the muscle fascia, providing for the controlled release of muscle relaxants and other therapeutic agents that may help to treat the syndrome as the therapeutic agents diffuse away from the containment device. Plantar Fasciitis, which is an inflammation of the plantar fascia tissue at its attachment to the heel bone, could also be treated through placement of the containment device near the plantar fascia (a tough, fibrous band of connective tissue that extends over the sole of the foot). Similar to the above examples, the containment device may provide for the controlled delivery of anti-inflammatory drugs and other therapeutic agents that may provide relief from the acute pain associated with the condition.

While the invention is susceptible to various modifications and alternative forms, specific examples thereof have been shown in the drawings and are herein described in detail. It should be understood, however, that the invention is to cover all modifications, equivalents, and alternatives falling within the scope of the appended claims.

What is claimed is:

1. A medical containment device for use in a bony body comprising:
   - a generally hollow body conformable to an interior cavity of a bony body, the generally hollow body having an opening through which a therapeutic material may be inserted, the generally hollow body providing a barrier preventing the unintentional migration of the therapeutic material from the interior of the generally hollow body; and
   - a delivery device to convey the generally hollow body into an interior of a bony body through an opening in the bony body, wherein the generally hollow body is attached to a distal end of the delivery device, and the generally hollow body has an actuator configured to deform the generally hollow body after the generally hollow body has been filled with the therapeutic material and before the generally hollow body is detached from the delivery device.

2. The medical device of claim 1, wherein the generally hollow body is made from a flexible or conformable material, sufficient to achieve optimal anatomic fit and clinical function.

3. The medical device of claim 1, wherein the generally hollow body has a pouch shape.

4. The medical device of claim 1, wherein the therapeutic material is a bone cement.

5. The medical device of claim 4, wherein the bone cement seals the containment device.

6. The medical device of claim 1, wherein the delivery device is a catheter.

7. The medical device of claim 1, further comprising a system to monitor healing.

8. The medical device of claim 1, wherein the delivery device comprises a junction of interlocking ends that is mechanically disconnectable.

9. The medical device of claim 1, wherein the opening of the generally hollow body is sealable.

10. A medical containment device for use in a vertebral body comprising:
    - a generally hollow body having an opening through which a bone cement may be inserted, the generally hollow body providing a barrier preventing the unintentional migration of the bone cement from the interior of the containment device; and
    - a delivery device to convey the generally hollow body into an interior of a bony body through an opening in the bony body, wherein the generally hollow body is attached to a distal end of the delivery device, and the generally hollow body has a ball valve actuator configured to deform the generally hollow body after the generally hollow body has been filled with the therapeutic material and before the generally hollow body is detached from the delivery device.

11. The medical device of claim 10, wherein the generally hollow body has a pouch shape.

* * * * *